United States Patent [19]
Jewell et al.

[11] Patent Number: 5,367,911
[45] Date of Patent: Nov. 29, 1994

[54] DEVICE FOR SENSING FLUID BEHAVIOR

[75] Inventors: Andrew D. Jewell, Bracknell; Michael A. Yuratich, Hamble, both of United Kingdom

[73] Assignee: Halliburton Logging Services, Inc., Houston, Tex.

[21] Appl. No.: 713,226

[22] Filed: Jun. 11, 1991

[30] Foreign Application Priority Data

Mar. 21, 1991 [GB] United Kingdom ............... 9105985.7

[51] Int. Cl.$^5$ ................................................. G01F 1/56
[52] U.S. Cl. .................................................. 73/861.08
[58] Field of Search ........... 73/861.32, 861.25, 861.08, 73/861.06, 304 C, 155; 324/687, 688, 690

[56] References Cited

U.S. PATENT DOCUMENTS

| | | | |
|---|---|---|---|
| 2,800,628 | 7/1957 | Stinson et al. | 324/690 |
| 3,221,248 | 11/1965 | Batteau et al. | 324/688 X |
| 3,437,924 | 4/1969 | Tocanne | 324/690 |
| 3,635,082 | 1/1972 | Prellwitz et al. | 324/690 X |
| 4,145,924 | 3/1979 | Muller | 73/861.06 |
| 4,568,874 | 2/1986 | Kramer et al. | 324/688 |
| 4,674,336 | 6/1987 | Johnston | 73/861.25 |
| 4,689,991 | 9/1987 | Beckley et al. | 324/690 X |
| 4,841,780 | 6/1989 | Inada et al. | 73/861.06 |
| 4,924,702 | 5/1990 | Park | 324/690 X |
| 4,947,683 | 8/1990 | Minear et al. | 73/861.25 X |
| 4,963,019 | 10/1990 | Foster et al. | 73/861.06 X |
| 5,052,223 | 10/1991 | Regnault et al. | 324/688 X |

*Primary Examiner*—Richard E. Chilcot, Jr.
*Assistant Examiner*—Elizabeth L. Dougherty
*Attorney, Agent, or Firm*—Arnold, White & Durkee

[57] ABSTRACT

A device (30) for sensing fluid behavior, e.g. flow, in a conduit (34) such as downhole in a well, comprises a tool (36) having two or more spaced sensors (38,40) for interacting with a medium within the conduit to produce data signals. The sensor data signals may be compared to determine movement of the medium within the conduit and about the device. The device is particularly suited for determining movement of multi-phase fluid.

19 Claims, 5 Drawing Sheets

DEVICE FOR SENSING FLUID BEHAVIOR

BACKGROUND OF THE INVENTION

1. Field of the Invention

The present invention relates to a method and apparatus for sensing fluid behaviour in a conduit, such as in a borehole. More particularly, but not exclusively, the present invention relates to measurement of multi-phase fluid flow within a borehole, and is of particular application to production logging and other in-hole flow measurement within well bores.

2. Description of Prior Art

Techniques are known for measuring the flow of fluids along pipelines, for example, utilizing sensors adjacent to, or incorporated in, the wall of the pipeline. Such sensors utilize one or another characteristic of the fluid in the pipeline to detect the movement of the fluid, and to produce output signals indicative of such movement. Such output signals may be processed as selected to provide information indicative of the fluid flow along the pipeline.

Such output information from two sensors may be cross-correlated to provide the flow information.

Figure 1:
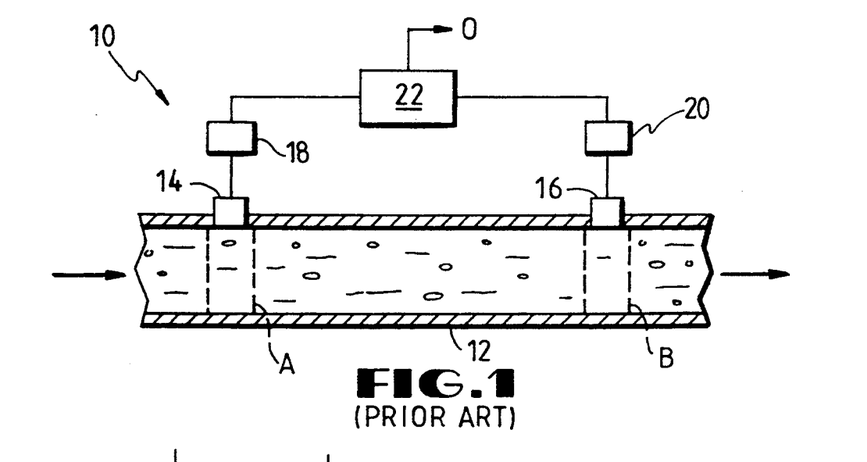
FIG. 1 is a schematic, fragmentary diagram of a prior art flowmeter including two sensors positioned for determining fluid flow along a pipeline which is shown in cross section.
Figure 2:
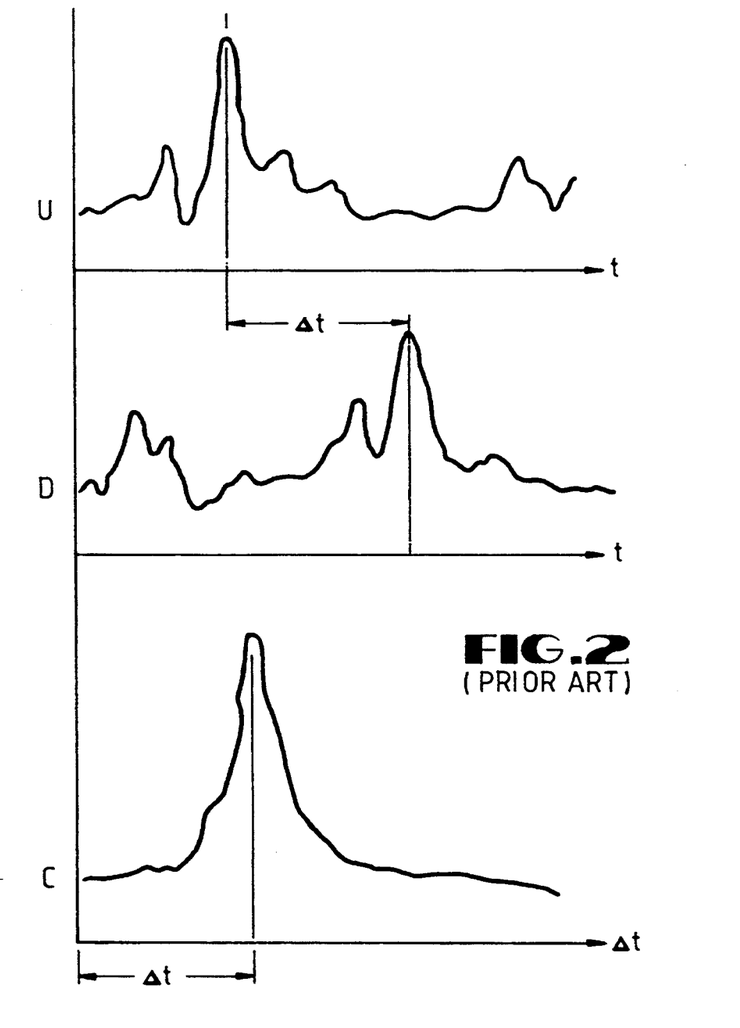
FIG. 2 is a graph of two suggested sensor signal traces, and a graph obtained by cross-correlation.

In the accompanying drawings, FIG. 1 is a schematic, fragmentary diagram of a prior art flowmeter including two sensors positioned for determining fluid flow along a pipeline which is shown in cross section; and FIG. 2 is a graph of two suggested sensor signal traces, and a graph obtained by cross-correlation.

Referring to FIG. 1, the prior art flowmeter is shown generally at 10, proportioned for determining flow of fluid within a pipeline 12. The arrows at the ends of the segment of the pipeline 12 indicate the direction of fluid flow within the pipeline. The fluid may be multi-phase, as generally indicated. Two sensors 14 and 16 are mutually displaced along the pipeline 12 so that one sensor 14 is upstream of the other sensor 16. Each of the two sensors 14 and 16 is exposed to, and takes measurements within, a sampling volume within the pipe 12. As indicated schematically, the upstream sensor 14 samples within volume A, and the downstream sensor 16 samples within volume B. The sensors are chosen to measure, or sense, some induced or intrinsic physical property of the flowing mixture of material within the pipe 12. Each sensor produces an output signal indicative of the measured physical property of the flowing media. The output signals may be processed, or reduced, as selected to provide data signals including information indicative of the flow of material in the respective sampling volumes A and B. The two data signals may then be cross-correlated. In the flowmeter of FIG. 1, the output signal of the upstream sensor 14 is initially processed in circuitry 18, and the output signal of the downstream sensor 16 is initially processed in circuitry 20. Data signals from the processing circuitry 18 and 20 are directed to a processor 22 which cross-correlates the data signals.

FIG. 2 indicates, generally schematically, data signals obtained indirectly from the upstream and downstream sensors. The data signals in each case are characteristic of the mixture sensed at the time in the respective sample volume within the pipe. For purposes of illustration, a significant peak is shown in the upstream data signal U. A similar, corresponding peak occurs in the downstream signal D at a time t later. The time t is the time required for the volume of material which produced the peak in signal U, when within the sample volume A, to move downstream into the sample B to produce the peak in the downstream signal D.

It will be appreciated that, as the fluid moves along in the flow, the particles and the components of the fluid will retain their relative positions only momentarily. Consequently, a sensor "image" of the sample area encompassing the same, or essentially the same, portion of the fluid, will vary, depending on how much later the second sensor detects, or reads, the sample. The time lag is, of course, related to the longitudinal speed of the fluid flow as well as the longitudinal separation between two sensors whose output is being compared. Additionally, the nature of the flow, e.g. its degree of turbulence, affects the rate at which the configuration of the fluid within the volume changes as the volume of fluid moves downstream. The nature of the flow, in turn, is dependent on characteristics of the fluid as well as the pipeline, or flow container. Consequently, the signal images produced by two sensors, one downstream of the other, when detecting the passage of the same segment of fluid will not be identical; on the contrary, the signal images will differ depending on the variation in the configuration of the segment of the fluid flow as that segment is detected by each of the two sensors. Consequently, it may be difficult to distinguish a profile feature of one sensor signal, characteristic of the fluid configuration sampled, and identify that same signal profile in the output signal from the downstream sensor based on the latter's detection of the same segment of the fluid. Consequently, the time of passage of the fluid between the sensor positions may not be readily determined by simply comparing output plots of the two sensor signals.

One way of making the comparison is to use so-called cross-correlation to determine the time delay in fluid flow between two sensors which are displaced relative to each other. The cross-correlation technique includes taking samples of the two signals to be compared, and shifting one signal sample relative to the other on a time scale, multiplying the two signals together and taking the average of the result. The cross-correlation output will generally not show any pronounced structure assuming the output signals are not periodic. However, when the signal time shift matches the actual time delay, that is, the time required for the segment of the fluid to flow from one sensor to the other whereby the two signals being compared were obtained by the respective sensors detecting the same fluid segment, the correlation process effectively multiplies the signal by itself, thereby calculating the mean squared value of the original signal to produce a pronounced peak in the cross-correlogram. The time shift of one signal relative to the other, required to obtain this maximum correlation output, identifies the fluid flow time delay, that is, the time for a segment of fluid to flow the distance of separation of the two sensors. Since this distance may be known, a calculation of the flow speed is readily made.

Correlation flowmeters are known for use with pipelines whereby the flowmeter apparatus is exterior to the pipeline with, in some cases, the sensors being directly exposed to the flow by being placed in the pipeline wall, for example. We have now devised apparatus for sensing fluid behaviour in a conduit, which device can be used as a flowmeter within a conduit, or tubular member, along which fluid may flow, with the flowmeter contained within the conduit, at least in part. Further, in accordance with the invention, the apparatus can be used for obtaining flowmeter measurements within a pipeline without the need for flowmeter apparatus exterior to, or even within the wall of, the pipeline at the location at which measurements are taken.

SUMMARY OF THE INVENTION

According to the present invention, there is provided apparatus for sensing fluid behaviour within a conduit, comprising:
a) a tool for positioning within such a conduit to establish a generally annular flow passage surrounding the tool and within the conduit;
b) an array of at least two sensors for detecting a characteristic of material in the annular flow passage with each sensor being positioned relative to the tool to detect material in a selected location relative to the tool, and which sensors generate output signals indicative of the material characteristics detected; and
c) a data reception system that receives the output signals of the sensors.

The invention further includes the use of such an apparatus for sensing fluid behaviour in a conduit.

In a preferred embodiment, the apparatus of the invention comprises a flowmeter, including a housing or tool, which may be positioned within a conduit such that the medium or material whose movement is to be determined may generally circumscribe the housing. The flowmeter includes at least two sensors which can interact with the medium to produce output signals indicative of the medium. The sensors may be mutually axially and/or circumferentially displaced about the generally elongate housing of the flowmeter. Further, the sensors may be relatively focussed to interact with well-defined segments of the medium. Each sensor may provide an output data signal indicative of the measured medium in the focus segment of the respective sensor.

The sensors may include acoustic transducers, or electrical conductivity (or resistivity) sensors. An electrical conductivity sensor may include a current-sensing electrode circumscribed, at least in part, by one or more guard electrodes to focus the region of the fluid medium through which current flow will pass, and therefore be sensed by the current-sensing electrode. A focussed electrical conductivity sensor according to the present invention may include a low resistivity, high impedance surface to which one or more low impedance current feeds connect to produce measure points which are relatively small areas of the sheet.

BRIEF DESCRIPTION OF THE DRAWINGS

In order that the invention may be more fully understood, various embodiments thereof will now be described, by way of example only, with reference to the accompanying drawings, wherein.

DESCRIPTION OF PREFERRED EMBODIMENTS

Figure 3:
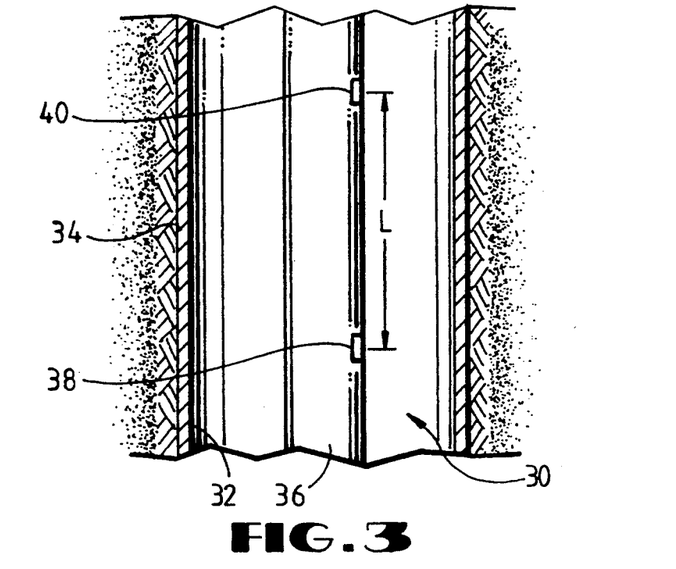
FIG. 3 is a schematic, fragmentary side elevation of one embodiment of flowmeter according to the present invention, shown positioned within a borehole.

One embodiment of a cross-correlation flowmeter according to the present invention is shown generally at 30 in FIG. 3, positioned within a borehole 32 lined with casing 34. Alternatively, or in addition, for example, the flowmeter 30 may be located within a production pipeline, or some other tubing string or pipeline. The flowmeter 30 is configured as part of a tool 36 which may be generally cylindrical. The flowmeter tool 36 may be incorporated within a production string used to remove oil and/or gas from a well or other tubing such as a drill string. The flowmeter tool 36 may also be provided in the form of a sonde, positioned within a borehole, supported by a wireline or other appropriate flexible connector.

The flowmeter 30 is shown including two sensors 38 and 40, mutually displaced a distance L, center-to-center, longitudinally along the tool 36. Configured in this fashion, the sensors 38 and 40 may be used to detect multi-phase flow longitudinally along the borehole 32, and either upwardly or downwardly. The sensors 38 and 40 are selected for their ability to respond to some physical property of matter in the borehole 32, and thus interact with fluid in the borehole. The sensors thus detect the fluid. If the fluid property to which the sensor responds is varied, this will be observable due to the corresponding change in any output signals generated by the sensors. As noted above, the time recordings will differ due to the travel time between the sensor sampling volumes, and specifically the flow development during that travel time. However, the statistical properties of the fluid flow will not change substantially during the travel time. For example, a gas bubble or a burst of fine solids will manifest itself in some way in both sampling volumes. The resulting similarity in the plots of the output signals of the two sensors, based on the detection of the same fluid flow segment in the two sampling volumes, is utilized in the cross-correlation of the flow recordings, as discussed above. The correlogram, that is the trace resulting from the cross-correlation of the two sensor data signals, ideally exhibits maximum value when one such sensor data signal is time-displaced relative to the other sensor data signal corresponding to the time required for the measured fluid flow segment to traverse the distance L. (As is known in the art, in practice there can be problems of interpretation.) The relative time-displacement between data output signals may be effected, in the cross-correlation process, in either sense, that is, both positive and negative, corresponding to fluid flow either upwardly or downwardly in the borehole 32. A case of zero net flow along the distance L may be confirmed by observing the time record of a single sample volume. Where the time variation of the signal at a sensor does not significantly change over an extended period of time, relatively speaking, it may be concluded that the lack of activity is an indication of zero net fluid flow.

Electronic circuitry to process data signals from sensors of a flowmeter according to the present invention may be included in the flowmeter housing positioned within a conduit, or may be maintained external to the conduit, that is, at the surface in a case of borehole flow measuring. Thus, the cross-correlation of the processed data signals may also occur in real time, either downhole for subsequent transmission or at the surface. Further, data signals and/or cross-correlograms may be maintained in memory within the flowmeter housing and retrieved when the flowmeter is removed from the conduit, for example.

One of the physical properties detectable by an appropriate sensor is the conductivity, or resistivity, of the fluid in the borehole. Thus, the various components of the fluid mixture may exhibit different conductivities. Such a multi-phase fluid distribution in particular, flowing along the casing 34, can readily produce structured time recordings of the data output signals of the sensors 38 and 40 for use in the cross correlation process.

Figure 4:
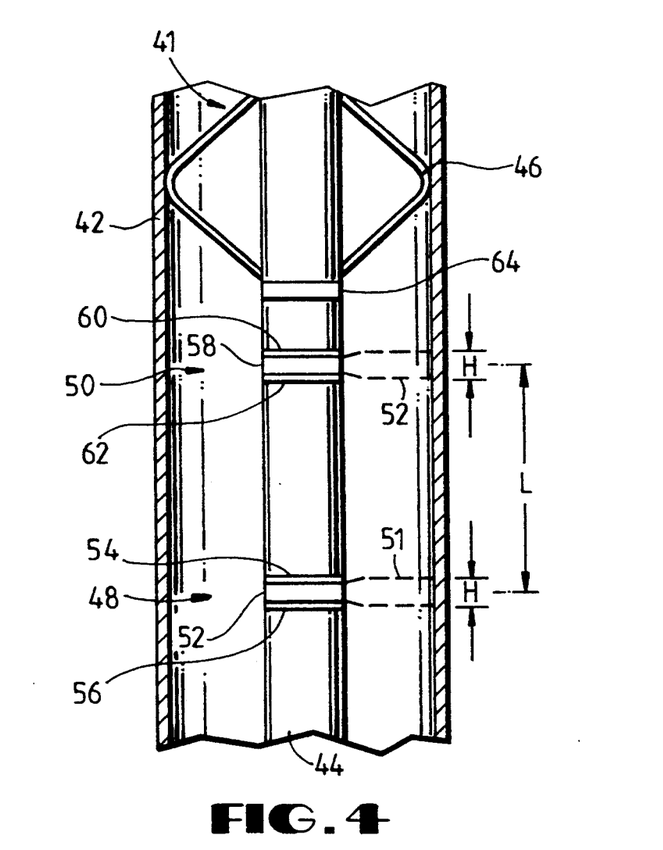
FIG. 4 is a view similar to FIG. 3, but illustrating an embodiment of a conductivity flowmeter according to the present invention.

A conductivity flowmeter according to the present invention is shown generally at 41 in FIG. 4, positioned within a borehole lined with a conductive casing 42. The flowmeter 41 is constructed with a tool body 44, and may be maintained generally centered within the casing 42 by use of known centralizers. For example, at least three circumferentially arranged bow springs for each centralizer can be used. Electrical contact can be provided between the casing and the tool by any suitable means, e.g. by using metallic centralizers. Two electric current sensors are shown generally at 48 and 50, arranged a longitudinal distance L apart along the tool body 44, and both below the centralizers 46. As discussed more fully below, a conductivity or resistivity, transducer is formed in the case of each of the sensors 48 and 50 utilizing a closed loop including, in each case, the sensor in question, the surrounding casing 42, the centralizers 46 and circuitry within the tool body 44. Each such closed loop relies on the conductivity of the fluid mixture in the annular region between the exterior of the tool body 44 and the interior surface of the casing 42. Electric current flow about the closed loop in question thus depends on the conductivity of the fluid mixture within the sample volume of the respective conductivity sensor.

The sample, or measuring, volumes of the fluid flow for the sensors may be controlled by focussing the sensors. In the case of the conductivity, or resistivity, sensors 48 and 50, focusing is accomplished by guard electrodes. The lower sensor 48 includes a current measurement electrode 52 flanked by insulation 54 and 56, the tool body 44 acting as guard electrode. The measuring electrode 52 is shown to include a conducting strip, lying in line with the exterior surface of the tool 44, and forming at least a portion of an annular band about the tool. The measuring electrode 52 "sees" the fluid surrounding the tool body 44 and the casing 42 beyond through a window defined, at least in part, by tool body 44 acting, on each side of insulation bands 54 and 56, as a guard electrode maintained at a fixed electric potential. The resulting sample volume is an annular disc S1, longitudinally centered on the measuring electrode 52, and extending outwardly at an axial height H similar to that of the electrode, as generally illustrated in FIG. 4. The current flow from the measuring electrode 52 effectively occupies the volume approximately H high. This current flow through the electrode 52 may be measured to produce the output data signal of the sensor 48.

The construction of the upper current sensor 50 resembles that of the lower current sensor 48. Thus, the upper current sensor 50 includes a current measuring electrode 58 in the form of a strip partially or entirely encircling the tool body 44, and flanked on opposite sides by insulation 60 and 62, with the body 44 constituting guard electrodes outside the insulation. The body 44 constituting the guard electrodes is maintained at a fixed potential, and the resulting sample volume S2 measured by the current electrode 58 circumscribes in whole or in part the tool body 44, and extends to a relatively uniform height H, generally as illustrated. The current flow through the electrode 58 and the adjacent fluid volume of height H may be measured to produce the output signal of the sensor 50.

Instead of using tool body 44 as the guard electrode, separate such electrodes can be provided adjacent the insulation bands (54,56,60,62).

A band of insulation 64 separates the surface of the tool body 44 including the current sensors 48 and 50 from the upper portion of the tool body carrying the centralizers 46.

With the two conductivity sensors 48 and 50 axially displaced as shown in FIG. 4, the dynamic range of the flowmeter 40 may be increased by increasing the spacing L. The sensitivity of the flowmeter 40 may be increased by increasing the focus width, or height H. These parameters may be varied while the flowmeter is downhole by constructing the flowmeter with an axial array of a greater number of conductivity sensors.

Figure 5:
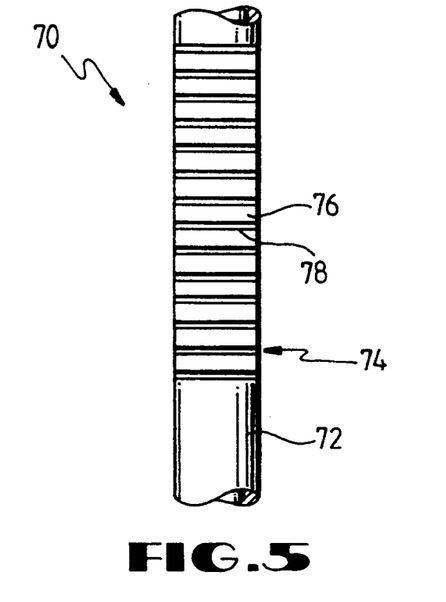
FIG. 5 is a fragmentary, side elevation of a conductivity flowmeter with an array of sensing electrodes arranged longitudinally along the flowmeter.

FIG. 5 illustrates a portion of a flowmeter 70, having a housing, or body 72, and equipped with an extended array of conductivity sensors indicated generally as 74. Each of the conductivity sensors 74 includes a current-sensing electrode 76 flanked by insulation 78. At each end of the array of sensors, the tool body 72 constitutes a guard electrode. In an alternative arrangement, individual guard electrodes can be provided between each electrode 76 in the array, with insulation separating adjacent electrodes. Each guard electrode would then contribute to the focus of current-sensing electrodes 76.

The longitudinal array of conductivity sensors 74 as shown in FIG. 5 may be operated in a variety of ways to achieve different effects. For example, any two of the current-sensing electrodes 76 may be utilized to obtain output signals which are then cross-correlated to determine the time for fluid to flow along the body 72 a distance equal to the separation between the selected current-sensing electrodes. Thus, a spacing L and focus width H may be determined for the two selected electrodes 76. The spacing L may be varied by varying the selection of current-sensing electrodes 76. The maximum value for L is then achieved by selecting two current-sensing electrodes 76 at opposite ends of the axial array of sensors 74; any other combination of two current-sensing electrodes 76 yields a smaller value for the spacing L.

The output signals of two or more sensors 74 may be added to produce a single, combination output signal. For example, two adjacent current-sensing electrodes 76 may have their conductivity measuring output signals combined. The effect of such a combination is to measure the conductivity across the focused measuring regions for each of the two electrodes 76. The two electrodes are effectively combined into a single current detector with a focus height H that is increased compared to the focus height for each individual sensor electrode 76, that is, the focus heights are added, or combined (they may overlap or be spaced apart) for the two sensors whose output signals are so combined. When individual guard electrodes are provided in the array as described above, the focus height H for each electrode may be varied depending on the width of the current-sensing electrode 76 and, therefore, the spacing of the guard electrodes on each side thereof. Consequently in the array of the sensors 74, the measuring regions for the individual current-sensing electrodes 76 may overlap axially, may be spaced to provide gaps therebetween, may be effectively butted against each other (when individual guard electrodes are present), may be of differing widths, or heights, and the array in general may provide focus heights with some or all of these features.

With an array of current sensors 74 as illustrated in FIG. 5, for example, the values of L and H for the flowmeter 70 may be varied while the flowmeter is positioned within a borehole by selectively switching the circuitry associated with the flowmeter. For example, the current loop associated with each of the sensors 74, as discussed above, may be selectively opened or closed to enable or disable individual sensor electrodes 76. Also, the output signals from the current-sensing electrodes 76 may be selectively combined to produce output signals for cross-correlation as discussed above.

In addition to the values of L and H being varied, the flowmeter 70 may be further manipulated even while positioned within a borehole, to provide two or more independent flowmeters. Thus, for example, any two current-sensing electrodes 76 may be operated and have their output signals cross-correlated to provide one flow velocity determination; at the same time, another pair of current-sensing electrodes 76 may be formed by cross-correlating their respective output signals for another flow velocity determination. It will be appreciated that one current-sensing electrode may be utilized in two such flowmeter arrangements. Thus, for example, three current-sensing electrodes 76 may be variously joined to provide three different flowmeter arrangements, and a multiple correlation technique, such as semblance processing, applied to better resolve the flow components.

The azimuthal, or circumferential, variation in fluid flow surrounding a flowmeter according to the present invention may be investigated by a circumferential array of two or more current-sensing electrodes. A flowmeter having such an arrangement of electrodes is shown generally at 80 in FIG. 6. Mounted on a flowmeter body 82 are two circumferential arrays 84 and 86 of conductivity sensors. The lower array 84 includes 4 current-sensing electrodes 88 (three are visible) positioned within (but insulated from) a guard electrode 90 in the form of a band circumscribing the housing 82. Each current-sensing electrode 88 is thus circumscribed by the guard electrode 90. Similarly, the upper sensor array 86 includes 4 current-sensing electrodes 92 (three are visible) similarly positioned to be circumscribed by a guard electrode 94 in the form of a band encircling the housing 82. It is to be understood that the number of current-sensing electrodes (88 and 92) need not be four but can be any number as is convenient and suitable to the intended use of the flowmeter.

Figure 6:
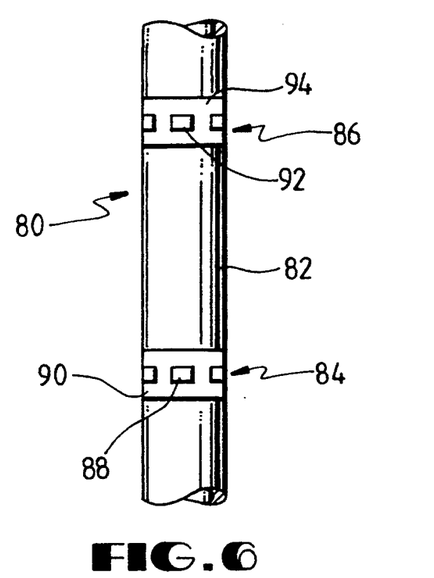
FIG. 6 is a view similar to FIG. 4, but showing an embodiment of a conductivity flowmeter with two sets of sensors having current-sensing electrodes in a circumferential array.

In an alternative construction, items 90 and 94 can constitute insulation in which case tool body 82 acts as guard electrode.

Figure 7:
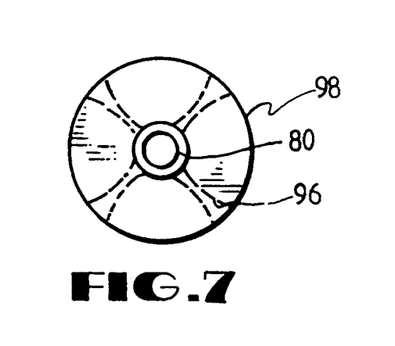
FIG. 7 is a schematic end elevation of the flowmeter of FIG. 6 showing focus measuring regions for the sensors.

FIG. 7 is a schematic representation in plan view of the flowmeter 80 at the axial position of the upper sensor array 86, shown circumscribed by the inner surface of a conduit 98. The lateral extent of the focus measuring region for each of the four current-sensing electrodes 92 is shown in FIG. 7 at 96.

Figure 8:
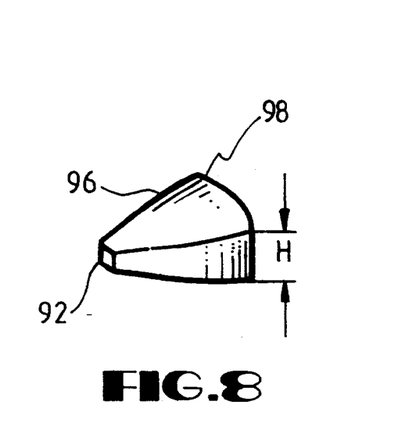
FIG. 8 is a schematic representation of such a sensor focus region, shown in perspective.

A perspective view of a focus region for one of the electrodes 92 is shown in FIG. 8. It will be appreciated from FIGS. 7 and 8 that each of the electrodes 88 and 92 measures conductivity by sensing current through a region of height H and azimuth of some selected degree. With four such current-sensing electrodes arrayed circumferentially at the same axial position, each electrode may be radially focussed to measure conductivity in an azimuthal extent of 90 degrees, for example, to provide measurements completely about the circumference of the housing 82.

The azimuthal extent of the focus of each current-sensing electrode 88 and 92 may be varied; further, the number of electrodes within a single circumferential array 84 and 86 may be varied and may be the same or different in each array. Consequently, the azimuthal extent of the focus regions may abut each other, may overlap, or may be spaced apart. Further, the value of H may be varied as discussed above by the construction of the individual electrodes. Also, whilst FIG. 6 shows electrodes 88 and 92 in alignment, this is not essential.

The current-sensing electrodes 88 and 92 of the flowmeter 80 may be combined in various ways to measure fluid flow within the region surrounding the flowmeter housing 82. For example, axial fluid flow may be measured by cross-correlating output signals from two electrodes 88 and 92 that are circumferentially, or azimuthally, aligned on the housing 82. Further, the output signals of all the electrodes 88 within the sensor array 84 may be combined to provide a single data signal which is then cross-correlated with a similar single data signal obtained from the combination of output signals of all of the electrodes 92 in the upper sensor array 86. Additionally, output signals of two circumferentially-spaced electrodes may be cross-correlated to measure fluid flow around the housing 82. For example, two current-sensing electrodes 88 in the lower array 84 may be enabled and their output signals cross-correlated. Similarly, an electrode 88 in the lower array 84 may have its output signal cross-correlated with the output signal from an electrode 92 in the upper array 86 wherein the two electrodes are not circumferentially aligned. Thus, fluid flow about the housing 82 may be measured in such fashion. It will be appreciated that some or all of the electrodes 88 and 92 may have their output signals cross-correlated, for example in pairs or in pairs of combinations. By examination of the resulting cross-correlograms, the nature of the fluid flow in the region surrounding the housing 82 may be determined by identifying the cross-correlograms showing the most well defined peaks. Thus, the actual flow path about the housing 82 may be determined and, from the selected cross-correlograms, the speed of that fluid flow may be quantitatively determined.

Figure 9:
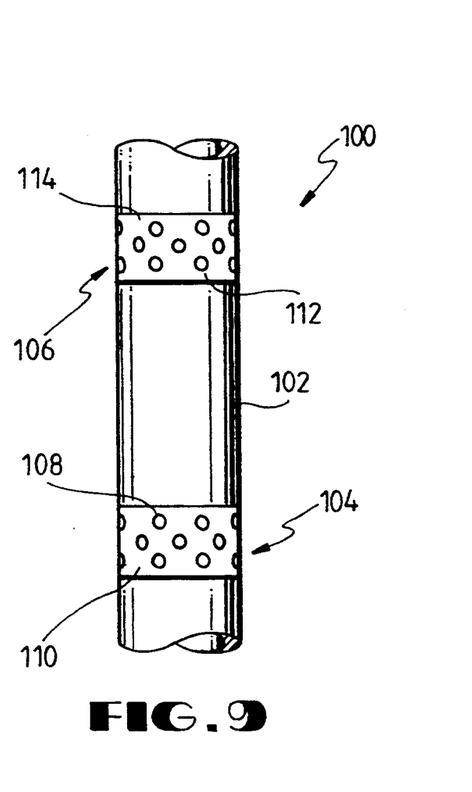
FIG. 9 is a view similar to FIG. 6, but illustrating an embodiment of a flowmeter having two arrays of a plurality of current-sensing electrodes, arranged both circumferentially and axially spaced within each array.

In addition to providing multiple, azimuthally arrayed electrodes in two axially displaced arrays, the present invention also contemplates additional electrodes spaced along and about the flowmeter body. Effectively, an array of current-sensing electrodes such as illustrated in FIG. 5 may be combined with an azimuthal array of current-sensing electrodes, generally as shown in FIG. 6. One form of such a two-dimensional array of electrodes is illustrated in FIG. 9. A flowmeter 100, having a housing, or body, 102, features current-sensing electrodes arranged both axially-spaced and circumferentially-spaced. The current-sensing electrodes are shown arranged in two arrays 104 and 106. Thus, the lower sensor array 104 includes current-sensing electrodes 108 positioned so that each electrode is circumscribed by surface area of a guard electrode 110 in the form of a circumferential band about the housing 102. (Each electrode is insulated from the surrounding guard electrode.) Similarly, the upper sensor array 106 includes current-sensing electrodes 112, with each electrode 112 circumscribed by surface area of a guard electrode 114 in the form of a circumferential band about the housing 102. Each of the current-sensing electrodes 108 and 112 is focused, both radially and axially, by the corresponding guard electrode 108 and 112. The extent of focusing may be selected so that the entire region about the housing 102, at the level of a sensing array 104 or 106, may be "covered" so that fluid movement within such region may be detected. Alternatively, the construction shown can be modified in that the tool body 102 can constitute the guard electrode, and bands 110, 114 can be of insulating material or can be omitted if other insulation is provided to separate each electrode 108, 112 from the body 102.

It will be appreciated from the foregoing discussions in connection with FIGS. 5-8 that the output signals of the various current-sensing electrodes 108 and 112 of the flowmeter 100 of FIG. 9 may be combined in any selected manner to detect fluid movement about the housing 102.

Figure 10:
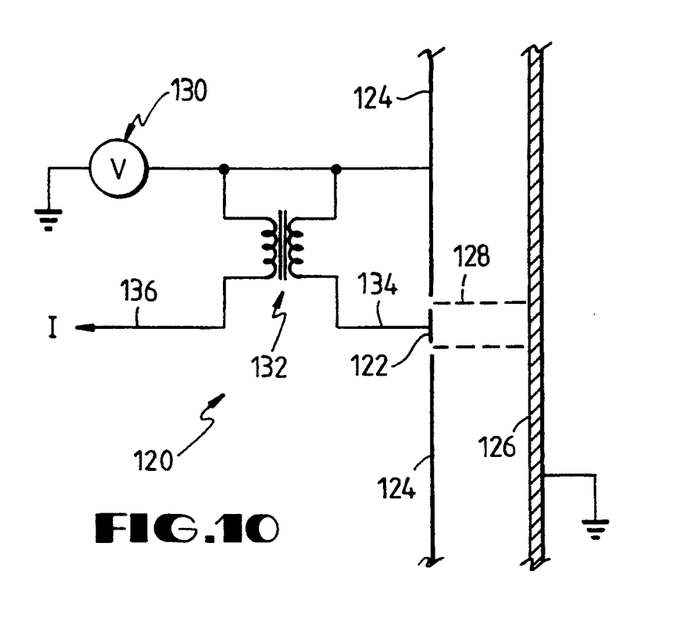
FIG. 10 is a circuit diagram of an embodiment of a conductivity sensor, focussed by guard electrodes, according to the present invention.

FIG. 10 illustrates a circuit diagram 120 for a focussed electrical conductivity sensor, or transducer. A current-sensing electrode 122 is insulated from but flanked by guard electrodes 124 and faces a conduit 126, such as a casing lining a borehole. The focus measuring region in the fluid between the electrode 122 and the conduit surface 126 is indicated at 128. A voltage source 130 maintains the guard electrodes 124 at constant potential, and is connected to the current-sensing electrode 122 through a transformer 132 and a line 134. Current flow across the fluid segment 128 to the conduit 126 is returned to ground, in practice by an electrical connection between the conduit and the flowmeter, such as by centralizers 46 illustrated in FIG. 4, for example. As the conductivity of the fluid within the measure segment 128 varies, the current through the electrode 122 varies accordingly. The variation in current in the line 134 through the transformer 132 to the conductor 122 operates through the transformer to generate a signal in a current output line 136. Thus, any variation of the conductivity of the fluid in the segment 128 is reflected in a corresponding current output signal in the line 136.

It will be appreciated that, with a voltage applied to the guard electrodes 124, current will flow through a conducting fluid positioned between the flowmeter and the conduit 126 through the guard electrodes 124 in addition to the current-sensing electrode 122. However, only the current flowing through the sensing electrode 122 is measured to provide the output signal from the line 136; therefore, only the current flowing through the focused region 128 is detected.

Figures 11, 12:
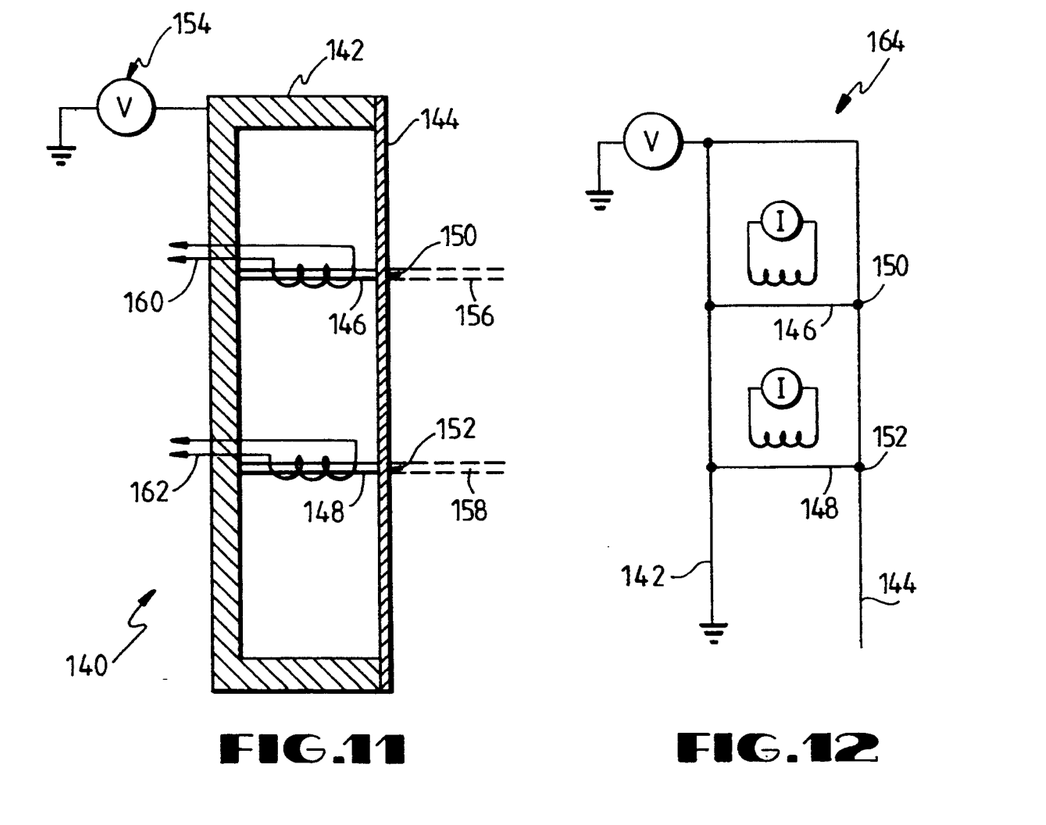
FIG. 11 is a schematic illustration of an embodiment of a multiple electrode conductivity sensor, utilizing a low resistivity surface with measuring points established thereon.
FIG. 12 is a circuit diagram of the conductivity sensor array of FIG. 11.

One example of a resistivity sensing transducer is illustrated in FIG. 11 at 140. Transducers of this sort are novel and are the subject of our U.S. Pat. No. 5,162,740, issued Nov. 10, 1992. The sensor 140 is a focused sensor, utilizing guard electrodes as discussed above. A sensor housing 142 is closed by a sheet 144 which, on a flowmeter body, is aligned with and forms a continuation of the outer surface of the body. Thus, the sheet 144 provides a "plane" in contact with the fluid medium between the sheet and the conduit surface generally circumscribing the flowmeter. Although the sheet 144 is composed of resistant material, and is in electrical as well as mechanical contact with the transducer housing 142, the resistivity of the sheet material is much lower than that of the fluid medium adjacent thereto and whose conductivity is to be measured.

One or more low impedance connectors contact the interior surface of the sheet 144 (in FIG. 11 two such connectors 146 and 148 are shown). The effective impedance of the resistive sheet 144 is much higher than that of the current feeds 146 and 148. The feed connectors 146 and 148 define two measure points 150 and 152, respectively, on the resistive sheet 144. The remainder of the sheet 144 operates as a guard electrode, surrounding the measure points 146 and 148, which form current-sensing electrodes.

In practice, a voltage supply 154 applies potential to the housing 142, and, therefore, to the resistive sheet 144. The potential thus generated across the fluid medium between the resistive sheet 144 and the oppositely-facing surrounding conduit surface (not shown) causes current to flow across that medium. However, the low impedance current feeds 146 and 148 enable the measure points 150 and 152 to act as individual electrodes, focused in measuring regions 156 and 158, respectively, by the surrounding surface of the sheet 144. Consequently, current flowing through the fluid in these regions 156 and 158 may be sensed, and measured by the corresponding current flow in the current feeds 146 and 148, respectively. Toroidal coils 160 and 162 circumscribe the current feeds 146 and 148, respectively, and provide circuit components through which the current variation through the measure regions 156 and 158 are reflected. Consequently, the coils 160 and 162 provide output signals from the measure points 150 and 152.

FIG. 12 shows a circuit diagram 164 for the transducer 140 for FIG. 11. It will be appreciated that a closed loop circuit, including the measure point 150 is completed by the measure point, the conducting fluid in the region 156, the surrounding conduit (not shown) connected electrically to the flowmeter by a centralizer, for example, and ground within the flowmeter body, the voltage source 154, the transducer housing 142 and the current feed 146. A similar closed loop circuit exists for the second measure point 152.

Current sensing transducers such as 140 may be constructed with a variety of measure point configurations as well as a varying number of such measure points.

Figure 13:
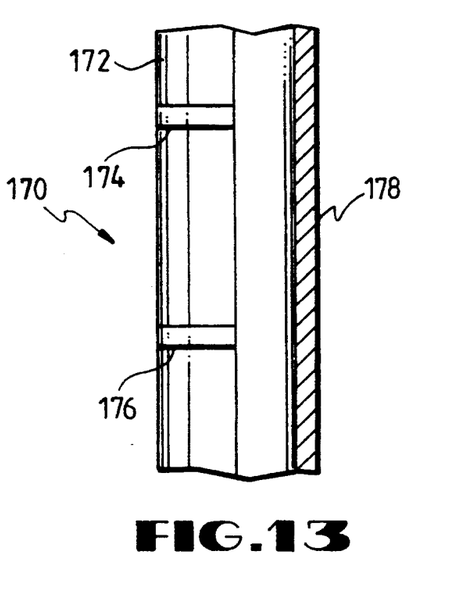
FIG. 13 is a schematic fragmentary side elevation of an embodiment of a flowmeter according to the present invention, utilizing acoustic transducers.

As noted above, virtually any sensor which interacts with the medium surrounding the flowmeter, depending on some physical property of the medium, may be utilized in a flowmeter of the present invention. Acoustical compression waves may interact with multi-phase fluid, for example, even including solid material. The backscatter and casing reflection, of an acoustic signal depend on the variation in acoustic impedance of the medium. FIG. 13 illustrates a portion of a flowmeter 170 according to the present invention, featuring a housing 172 and two ultrasonic transducers 174 and 176 positioned axially displaced along the housing. The flowmeter 170 is shown opposite a segment of a conduit 178 within which the flowmeter is positioned. The transducers 174 and 176 are indicated schematically, and may be either annular or composite transducers, for example. An acoustic wave is transmitted by the upper transducer 174, and travels through the surrounding fluid medium to the conduit 178. The wave is reflected from the conduit 178 back to the flowmeter body 172, where it is received by the same transducer 174 or a closely adjacent one (not shown). Similarly the lower transducer 176 emits an acoustic wave which travels to, and is reflected by, the conduit 178 to be received by the same transducer, or a closely adjacent one (not shown).

The invention will be described with reference to the use of ultrasonic pulses as the acoustic means, but pulses or other time-varying waves such as swept frequency waves may be used as will be understood in the art.

As an acoustic pulse wave is transmitted through the medium between the flowmeter 170 and the conduit 178, the wave is reflected by changes in the acoustic impedance of the medium, so that, particularly in a multi-phase medium, a reflected wave is generally continually generated to be received back at the flowmeter. The greatest reflection may be expected to be caused by the conduit 178, since the conduit is a hard solid. Nevertheless, the varying impedance of the medium at the axial position of the measuring transducer 174 or 176 provides a signature profile in the output signal of the acoustic transducer. Thus, each of the two axially spaced acoustic transducers 174 and 176 provides an output signal which is indicative of the medium at the level of the sensor when the signal is formed. Thus, the output signals from the two acoustic sensors 174 and 176 may be cross-correlated to determine the time required for the fluid medium to move between the position of one of the sensors and the other.

Figure 14:
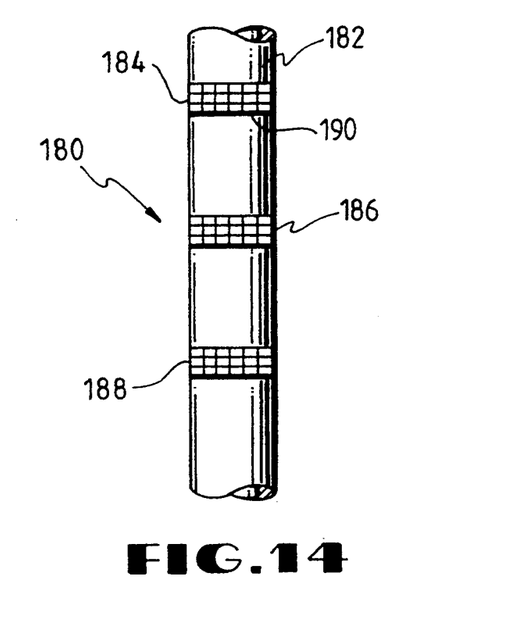
FIG. 14 is a view similar to FIG. 13, but showing an embodiment of a flowmeter with arrays of axially and circumferentially spaced acoustic transducers.

As in the case of the conductivity detectors discussed above, various arrays of acoustic transducers may be constructed to allow dynamic and sensitivity adjustment of the flowmeter characteristics as well as measurement of azimuthal profiles. FIG. 14 illustrates an acoustic transducer flowmeter 180, having a housing 182 and three axially spaced transducer arrays 184, 186 and 188. Within each of the three transducer arrays there exists a plurality of acoustic transducers 190 arranged in three axially spaced rows, and in each row, arranged azimuthally displaced. As in the case of the electrical conductivity sensors discussed above, the acoustic sensors 190 may be enabled and their output signals combined in any combination of two or more sensors. Thus, axial flow, azimuthal flow and spiral flow, for example, may be detected by cross-correlating output signals from various combinations of the sensors 190. The cross-correlograms providing the greatest peaks may be utilized to determine the direction of fluid flow as well as its speed about the flowmeter housing 182.

The acoustic wave generated by the acoustic transducers in flowmeters according to the present invention may be focussed by various means. For example, acoustic Fresnel lenses and electronic phasing of multiple transducers may be employed to selectively focus the acoustic waves.

A time record of a reflected acoustic wave contains radial information because of the finite velocity of the sound wave traversing the measured medium. This radial information provides a signature of the flow at various radius values through the medium. Consequently, an acoustic transducer focussed in one radial direction obtains an image, in time, of the fluid medium in the focus region. A circumferential array of acoustic transducers provides a two-dimensional profile of the flowing medium, and may be cross-correlated or otherwise processed.

Figure 15:
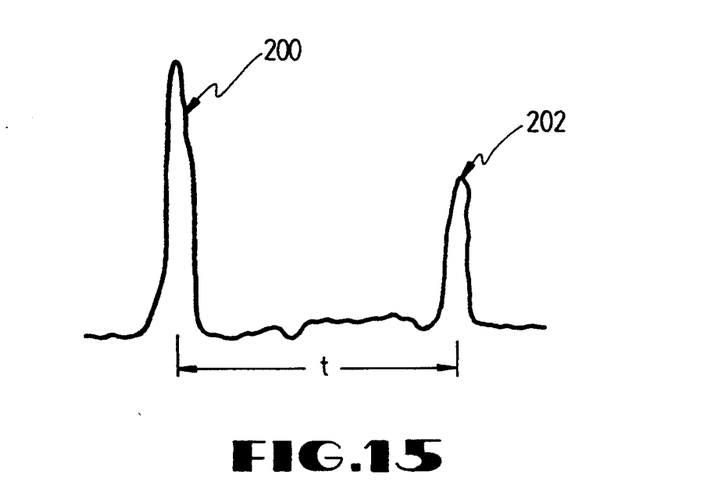
FIG. 15 is a plot of the output signal of an acoustic detector illustrating the identification of a reflection from a surrounding conduit.

Since the reflection by the conduit 178, for example, of an acoustic wave passing through the fluid medium may be expected to be of the greatest intensity of the reflections, the conduit may be used to provide a calibration of the acoustic wave in the radial direction for measurement purposes. FIG. 15 illustrates a sound wave that may be generated by one of the transducers of FIGS. 13 and 14, for example. The initial pulse generated by the transducers in question provides an initial peak 200. At some time T later, the transducer detects a significant reflection from the conduit 178, for example, and produces a significant peak 202 in the transducer output signal accordingly. The time T is the time for the acoustic wave to travel from the generating transducer to the conduit and back. The reflection peak 202 thus provides an absolute reference from which fractional radii may be deduced in analyzing the profile of the fluid between the flowmeter and the conduit. The conduit, or casing, reference may be obtained utilizing other time-varying sound waves, such as swept-frequency waves, for example.

The present invention thus provides a flowmeter for use remotely located within a conduit, and particularly suited for use in determining the flow of multi-phase fluid, for example. The flowmeter may utilize any type of sensor which interacts with the medium being measured, such as electrical conductivity sensors and acoustic sensors. The sensors may be arranged in various configurations to analyze and quantitatively measure movement of the fluid about the flowmeter and within the surrounding conduit wall. Two sensors provide the necessary measurement for the flowmeter to determine the medium flow speed. Output signals from the sensors may be cross-correlated for accurate determination of time intervals measured to determine the speed of fluid movement and the direction of the flow. The sensors may be focused to well-define the regions of the medium the sensors measure. The sensitivity and dynamic range of the sensors, and of the flowmeter in general, may be selectively varied. The apparatus of the invention can also be used to describe the fluid state in a deviated well.

The foregoing disclosure and description of the invention is illustrative and explanatory thereof, and various changes in the method steps as well as in the details of the illustrated apparatus may be made within the scope of the appended claims without departing from the spirit of the invention.

What is claimed is:

1. Apparatus for sensing fluid behavior within a conduit, comprising:
   (a) a tool positionable within said conduit for establishing a generally annular flow passage surrounding the tool within the conduit;
   (b) at least two sensors in an array for detecting characteristics of material in the annular flow passage with each sensor being coupled to said tool, which sensors generate output signals indicative of the material characteristics detected, and wherein at least one of said sensors is a conductivity sensor having an electrode circumscribed by and insulated from a surrounding conductive ring, wherein said fluid does not pass through the interior of said tool proximate said sensors; and
   (c) a data reception system operably coupled to receive the output signals of the sensors.

2. Apparatus according to claim 1, wherein in use the conduit cooperates with at least one sensor to form a part of a signal return.

3. Apparatus according to claim 1, wherein at least two of said sensors are mutually displaced longitudinally along said tool.

4. Apparatus according to claim 1, wherein at least two said sensors are mutually displaced circumferentially about said tool.

5. Apparatus according to claim 1, wherein at least one sensor generates output signals indicative of material in the annular flow passage at a predetermined radial location.

6. Apparatus according to claim 1, further comprising at least one electrical conductor line connected to one said electrode wherein in use said electrical conductor line, said electrode and material in the annular region between the tool and the conduit cooperate to provide, in part, a conducting loop; and a winding about said loop whereby an output signal may be conveyed depending on the conductivity of the material in the annular region.

7. Apparatus according to claim 1, further comprising a cross-correlation signal processor to which information indicative of output signals from at least two of said sensors is conveyed and which compares and correlates said information.

8. Apparatus according to claim 1, further comprising at least one electrical conductor line connected to one said electrode wherein in use said electrical conductor line, said electrode and material in the annular region between the tool and the conduit cooperate to provide, in part, a conducting loop for conveying a signal of the conductivity of the material in the annular region.

9. Apparatus according to claim 8 further comprising a cross-correlation signal processor to which information indicative of output signals from at least two of said sensors is conveyed and which compares and correlates said information.

10. Apparatus for sensing fluid behavior within a conduit, comprising:
    (a) a tool positionable within said conduit for establishing a generally annular flow passage surrounding the tool and within the conduit;
    (b) at least two focused transducers in an array for detecting characteristics of material in the annular flow passage external to said tool with each focused transducer being positioned coupled to said tool to detect material characteristics in a predetermined location relative to the tool, which transducers generate output signals indicative of the material characteristics detected and said transducers including a central electrode circumscribed by and insulated from a surrounding ring; and
    (c) a data reception system coupled to receive the output signals of the sensors.

11. Apparatus according to claim 10, wherein at least two of said transducers are mutually displaced longitudinally along said tool.

12. Apparatus according to claim 10, wherein at least two said transducers are mutually displaced circumferentially about said tool.

13. Apparatus according to claim 10, wherein at least one transducer comprises a focused conductivity electrode, carried by the tool, circumscribed by, and insulated from a surface of electrically conductive material.

14. Apparatus for sensing fluid behavior within a conduit, comprising:
    a tool positionable within said conduit for establishing a generally annular flow passage surrounding the tool and within the conduit;
    at least two sensors in an array for detecting characteristics of material in the annular flow passage external to said tool with each sensor being coupled to said tool to detect material characteristics in a predetermined location relative to the tool, which sensors generate output signals indicative of the material characteristics detected; and
    a data reception system that receives the output signals of the sensors; and wherein
    said sensors are focused conductivity sensors having,
    a central electrode,
    a surrounding conductor, and
    an insulating ring between said central electrode and said surrounding conductor.

15. Apparatus according to claim 14 wherein at least two of said sensors are mutually displaced longitudinally along said tool.

16. Apparatus according to claim 14 wherein at least two of said sensors are mutually displaced circumferentially about said tool.

17. Apparatus for sensing fluid behavior within a conduit, comprising:
    (a) a tool positionable within said conduit for establishing a generally annular flow passage surrounding the tool and within the conduit;
    (b) at least two sensors in an array for detecting characteristics of material in the annular flow passage external to said tool with each sensor being coupled to said tool, which sensors generate output signals indicative of the material characteristics detected, and wherein at least one of said sensors is a conductivity sensor having an electrode circumscribed by and insulated from a surrounding conductive ring; and
    (c) a data reception system that receives the output signals of the sensors, said data reception system coupled to said conduit wherein in use the conduit cooperates with at least one sensor to form a part of a signal path to said data reception system.

18. Apparatus for sensing fluid behavior within a conduit, comprising:
(a) a tool positionable within said conduit for establishing a generally annular flow passage surrounding the tool and within the conduit;
(b) at least two sensors in an array for detecting characteristics of material in the annular flow passage external to said tool with each sensor being coupled to said tool, and which sensors generate output signals indicative of the material characteristics detected, and at least one of said sensors is a conductivity sensor having an electrode circumscribed by and insulated from a surrounding conductive ring;
(c) at least one electrical conductor line connected to one said electrode wherein in use said electrical conductor line, said electrode and material in the annular region between the tool and the conduit cooperate to provide, in part, a conducting loop; and a winding about said loop to convey an output signal depending on the conductivity of the material in the annular region; and (d) a data reception system that receives the output signals of the sensors.

19. Apparatus for sensing fluid behavior within a conduit, comprising:
(a) a tool positionable within said conduit for establishing a generally annular flow passage surrounding the tool and within the conduit;
(b) at least two sensors in an array for detecting characteristics of material in the annular flow passage external to said tool with each sensor being coupled to said tool, and which sensors generate output signals indicative of the material characteristics detected, and at least one of said sensors is a conductivity sensor having an electrode circumscribed by and insulated from a surrounding conductive ring;
(c) at least one electrical conductor line connected to one said electrode wherein in use said electrical conductor line, said electrode and material in the annular region between the tool and the conduit cooperate to provide, in part, a conducting loop; and an output signal for forming a signal of the conductivity of the material in the annular region; and
(d) a data reception system that receives the output signals of the sensors.

* * * * *